(12) United States Patent
Greenfield et al.

(10) Patent No.: US 6,698,044 B2
(45) Date of Patent: Mar. 2, 2004

(54) PEDIATRIC STIRRUP DEVICE AND METHOD

(76) Inventors: Saul P. Greenfield, PMB 168 3380 Sheridan Dr., Amherst, NY (US) 14226; Julian H. Wan, PMB 168 3380 Sheridan Dr., Amherst, NY (US) 14226; Clifford P. Limpert, 11500 Madison Ave., Cleveland, OH (US) 44102

( * ) Notice: Subject to any disclaimer, the term of this patent is extended or adjusted under 35 U.S.C. 154(b) by 55 days.

(21) Appl. No.: 10/112,152

(22) Filed: Mar. 30, 2002

(65) Prior Publication Data

US 2003/0182726 A1 Oct. 2, 2003

(51) Int. Cl.[7] ............................................. A61G 13/12
(52) U.S. Cl. ................... 5/624; 5/649; 5/621; 248/104; 362/804; 362/427; 403/52; 403/57
(58) Field of Search .................. 5/624, 621, 622, 5/623, 649, 648, 650, 651, 646, 647, 603; 248/104; 362/804, 427; 403/52, 57, 374.3

(56) References Cited

U.S. PATENT DOCUMENTS

| | | | |
|---|---|---|---|
| 1,546,813 A | | 7/1925 | Thomsen |
| 1,894,739 A | | 1/1933 | Gilbert |
| 2,792,266 A | | 5/1957 | Waters |
| 3,180,600 A | * | 4/1965 | Kopec ........................ 248/104 |
| 3,355,163 A | | 11/1967 | Leinassar |
| 3,823,933 A | | 7/1974 | Mueller et al. |
| 3,907,270 A | | 9/1975 | Ezzo |
| 3,944,205 A | | 3/1976 | Mueller |
| 3,982,742 A | | 9/1976 | Ford |
| 4,023,757 A | | 5/1977 | Allard et al. |
| 4,209,012 A | | 6/1980 | Smucker |
| 4,733,836 A | | 3/1988 | Barnes |
| 4,809,687 A | | 3/1989 | Allen |
| 5,369,827 A | | 12/1994 | Parke et al. |
| 5,699,988 A | | 12/1997 | Boettger et al. |
| 5,935,061 A | | 8/1999 | Acker et al. |
| 6,289,537 B1 | | 9/2001 | Hopper et al. |

OTHER PUBLICATIONS

Mediflex Brochure (Date Unknown).

* cited by examiner

*Primary Examiner*—Alexander Grosz
(74) *Attorney, Agent, or Firm*—Fay, Sharpe, Fagan, Minnich & McKee, LLP

(57) ABSTRACT

A medical stirrup device includes a base adapted for fixed securement to an associated support member. The device further includes a gooseneck shaft member having a proximal end connected to the base and a distal end spaced from the base. The gooseneck shaft member is selectively manually bendable by an end-user into a curvilinear operative shape between an unbent linear position and a bendable limit of the gooseneck shaft member. A fastener is located at the distal end of the gooseneck shaft member. The fastener is adapted to engage a mating fastener of an associated limb support member to connect the associated limb support member to the shaft. In one version of the development, the shaft member includes first and second co-axial spiral-wound tubular members. In another version, the shaft has adjustable rigidity and is defined from a series of articulated links. A method of positioning a human limb for a medical procedure is also disclosed.

9 Claims, 4 Drawing Sheets

PEDIATRIC STIRRUP DEVICE AND METHOD

BACKGROUND OF THE INVENTION

The present development relates to a medical stirrup device and method for supporting patient limbs during surgery or other procedures. More particularly, the present development relates to a pediatric stirrup device for supporting the legs or arms of an infant or other small child during surgery or other procedures.

Medical stirrup devices are well known and in widespread use. Heretofore, medical stirrup devices have been provided in one of two forms. One prior device is exemplified by that disclosed in U.S. Pat. No. 3,982,742 to Ford. The Ford '742 patent discloses a medical stirrup device that utilizes an elongate curvilinear shaft to support foot/ankle straps. The shaft is said to be "flexible" but the shaft are preformed into the curvilinear shape and are not bendable or moldable into a different shape. To adjust the position of the foot/ankle strap and, consequently, the patient's limb supported thereby, the shaft is rotated. The shaft cannot be bent or otherwise shaped by an end-user during a procedure or otherwise.

Other stirrup devices are disclosed, e.g., in U.S. Pat. No. 3,944,205 to Mueller and U.S. Pat. No. 6,289,537 to Hopper et al. Here, various linkages and the like are used to adjust the position of the foot/ankle support. The Mueller '205 patent discloses a stirrup extension bar held in place during use by friction. The Hopper '537 patent also discloses a device that relies upon friction to hold the stirrup support shaft in a desired operative position.

These prior devices and others have been found to be unsuitable for use during pediatric procedures. In particular, these prior devices do not provide a convenient and effective means by which a physician, nurse or technician can infinitely adjust limb position prior to beginning or in the midst of a procedure. Also, these prior devices typically provide a completely rigid support that does not yield at all to increase comfort. Furthermore, with these prior devices, it is possible to set the stirrup in a position that results in over-extension of the patient's limb. In light of the foregoing, a need has been identified for a novel and unobvious medical stirrup device that overcomes the foregoing deficiencies and others while providing better overall results.

SUMMARY OF THE INVENTION

In accordance with the present invention, a medical stirrup device comprises a base adapted for fixed securement to an associated support member. A gooseneck shaft member includes a proximal end connected to the base and a distal end spaced from the base. The gooseneck shaft member is selectively manually bendable into a curvilinear operative shape between an unbent linear position and a bendable limit of the gooseneck shaft member. A fastening element is located at the distal end of the gooseneck shaft member. The fastening element is adapted to engage an associated mating fastening element of an associated limb support member to connect the associated limb support member to the gooseneck shaft member.

BRIEF DESCRIPTION OF THE DRAWINGS

The invention comprises various components and arrangements of components, preferred embodiments of which are illustrated in the accompanying drawings that form a part hereof and wherein.

DETAILED DESCRIPTION OF PREFERRED EMBODIMENTS

Figure 1:
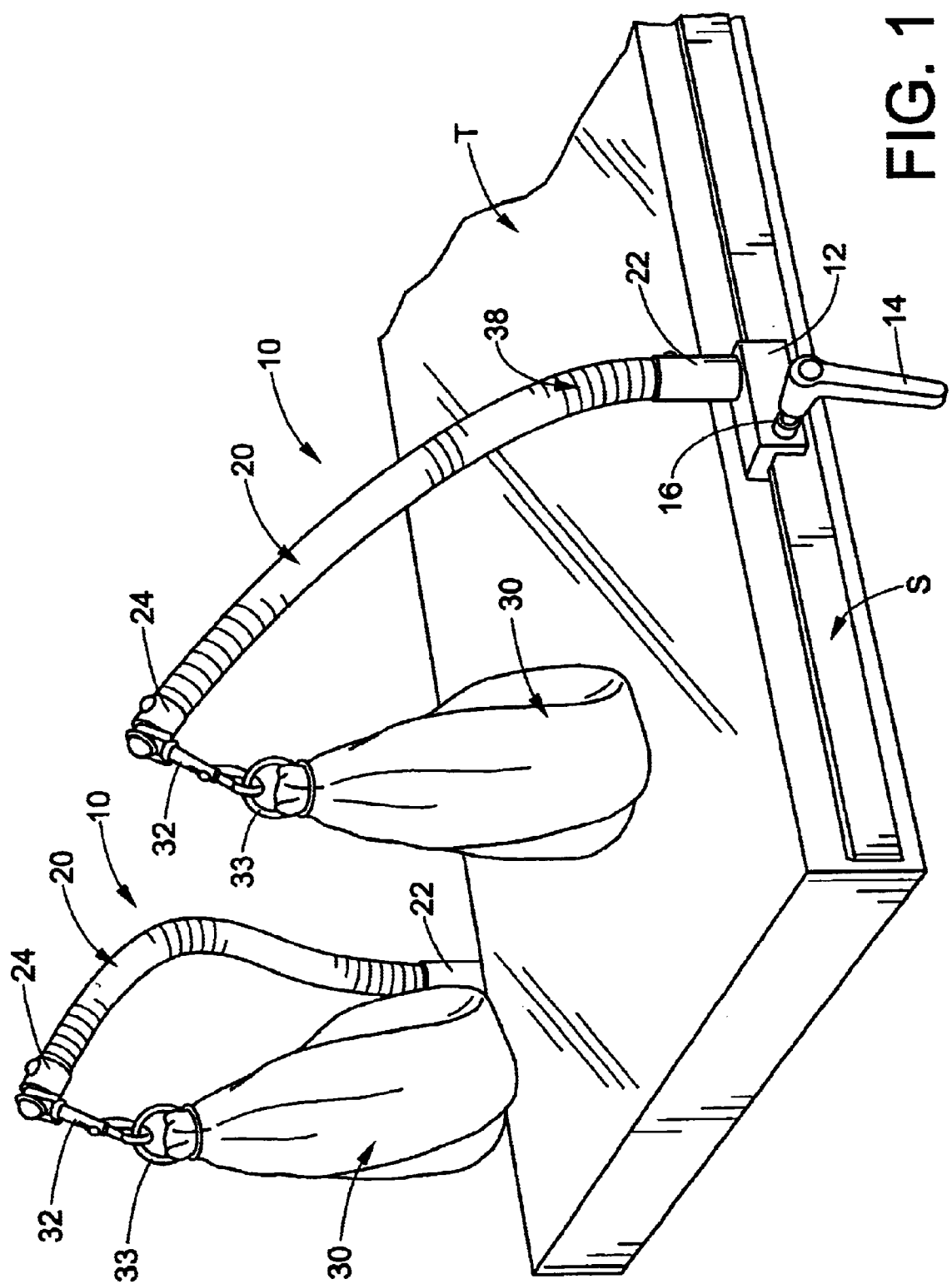
FIG. 1 is a perspective view of first and second stirrup devices formed in accordance with the present invention operatively secured to opposite lateral sides of a procedure table (with the table being only partially shown)

Referring now to the drawings, which are for purposes of illustrating preferred embodiments only and are not intended to limit the invention in any way, FIG. 1 illustrates first and second identical medical stirrup devices 10 formed in accordance with the present invention. Each device 10 comprises a base 12 adapted for connection to a side-rail S of a procedure table T or another suitable support member. A handle 14 is connected to a set screw 16 that is used to releasably fixedly secure the base 12 to the side-rail S in a desired operative position. A gooseneck shaft 20 includes a proximal end 22 connected to the base and a distal end 24 spaced from the base 10. A snap-hook, ring, split-ring, D-ring, clip, strap, hook-and-loop fastening element or other fastener or fastening element 32 is provided to mate releasably with a corresponding or mating fastener or fastening element 33 of a fabric loop or other limb support member 30 to the distal end 24 of the shaft 20. The limb support member 30 is adapted to receive and retain a patient's limb/foot/ankle/leg/arm etc. as is generally known. The limb support member 30, itself, is conventional in all respects and is omitted from FIGS. 2–5 for clarity.

Figure 2:
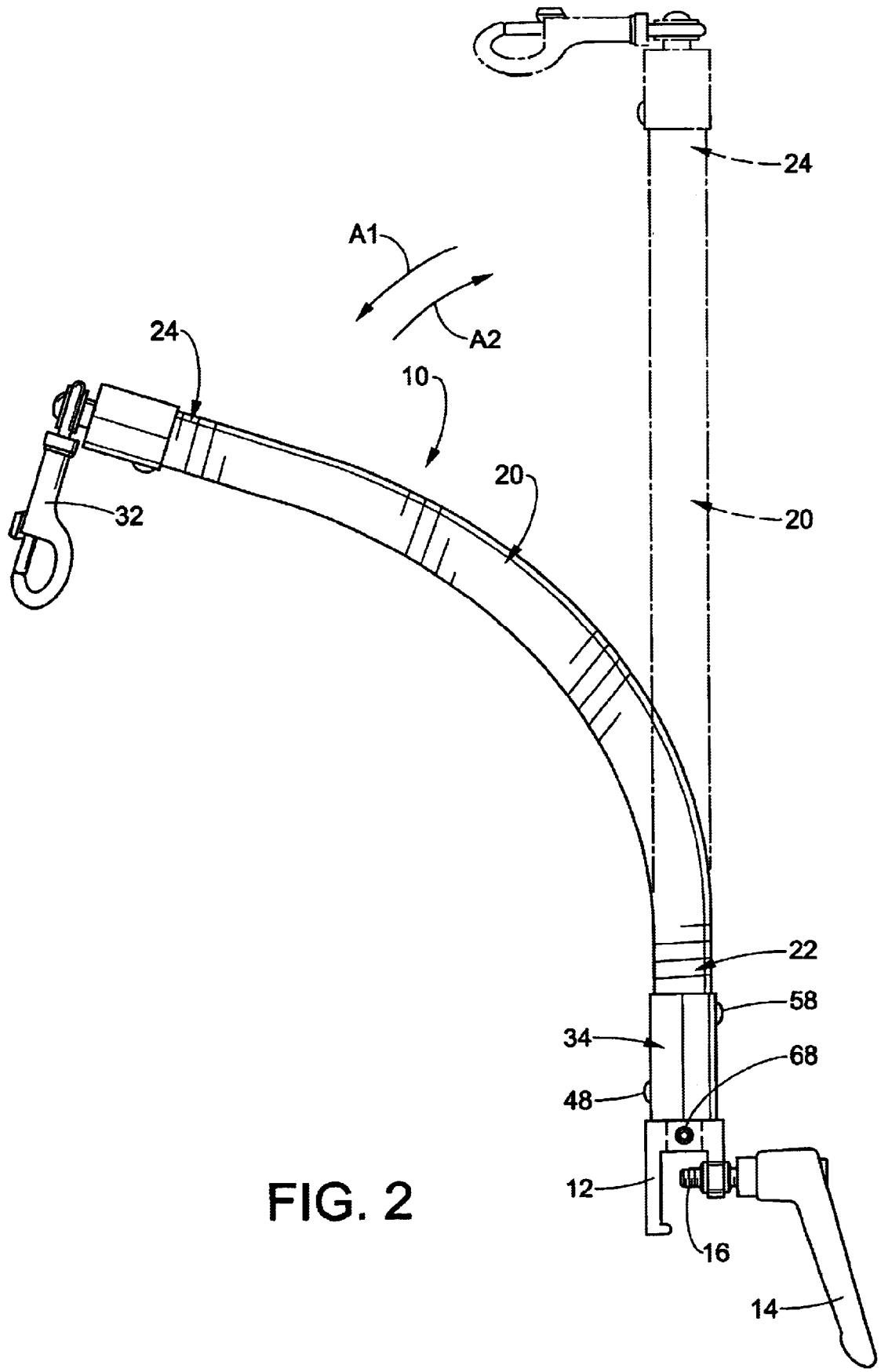
FIG. 2 is a front elevational view of a medical stirrup device formed in accordance with the present invention in first and second positions, with the first position shown in phantom lines to illustrate the adjustability of the device.
Figures 3, 4:
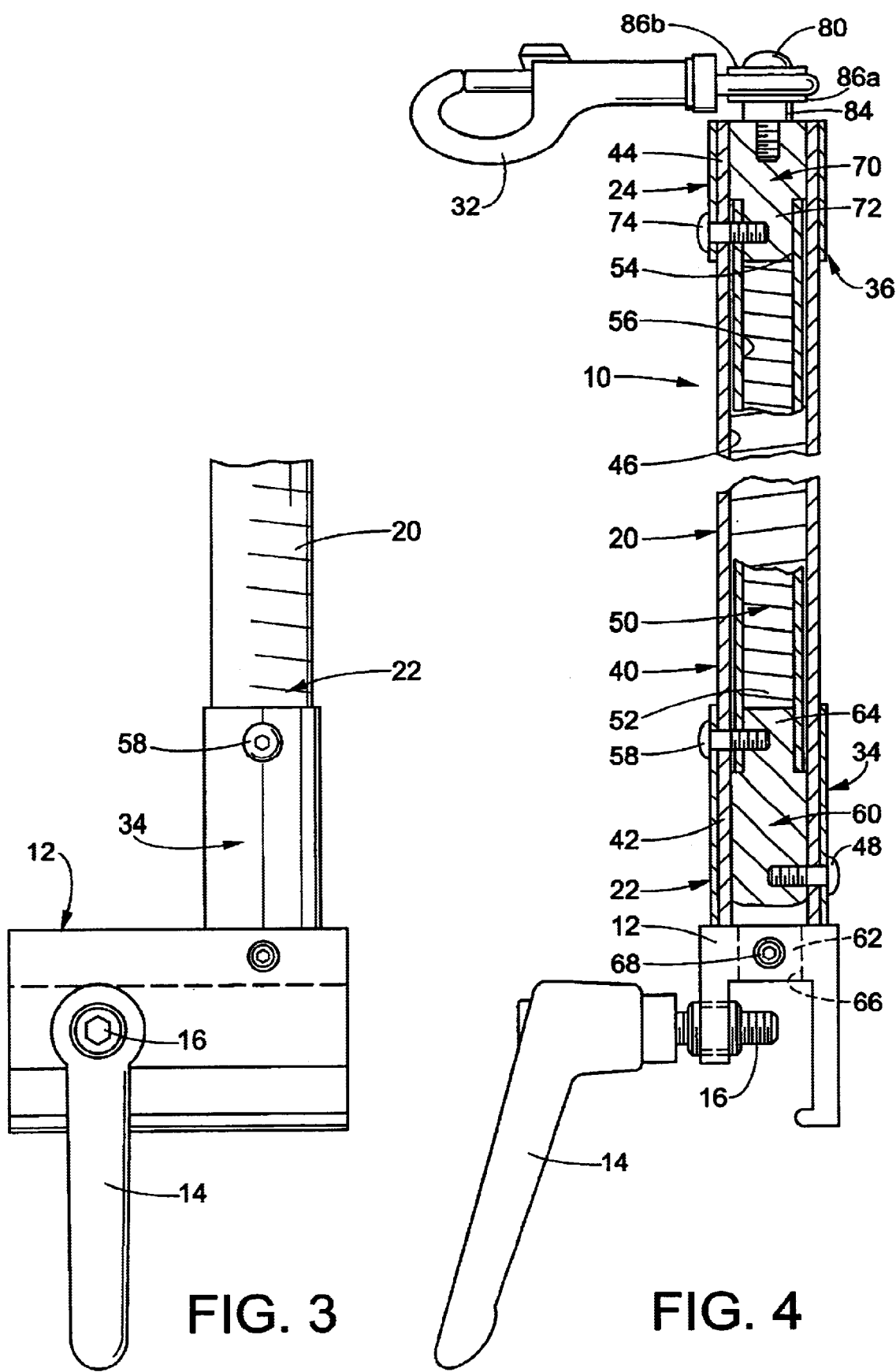
FIG. 3 is a partial side elevational view of the medical stirrup device of FIG. 2.
FIG. 4 is similar to FIG. 2 but illustrates the shaft of the medical stirrup device in section; and, FIG. 5 is similar to FIG. 4 but illustrates a medical stirrup device formed in accordance with an alternative embodiment of the present invention.

The medical stirrup device 10 is also shown in FIG. 2 and is partially shown in FIG. 3. There, it can be seen that the shaft 20 is made from gooseneck or other suitable material that is selectively flexible and/or bendable in any desired direction and into any desired position as indicated by the arrows A1, A2. The bendable limit that determines the range of motion for the shaft 20 is defined herein as the a point where further bending of the shaft 20 will damage the shaft and/or permanently deform the shaft). The bendable limit of the shaft 20 will vary depending upon the particular gooseneck material used to manufacture the shaft 20. The shaft 20 is bendable from a straight or unflexed position as shown in phantom to any desired curvilinear operative position such as that shown in solid lines up to the bendable limit of the shaft.

FIG. 4 illustrates a preferred embodiment of the medical stirrup device 10 wherein the shaft 20 comprises first and second gooseneck members 40,50. The first gooseneck member 40 comprises a proximal end 42 and a distal end 44. The second gooseneck member 50 comprises a proximal end 52 and a distal end 54. The first gooseneck member 40 defines a through-bore 46 in which the second gooseneck member 50 is positioned, in at least roughly a coaxial manner as shown. The second gooseneck member 50 also defines a through-bore 56.

The first and second gooseneck members 40,50 are fixedly secured to the base 12 by means of a first mounting stud 60. In the illustrated embodiment, the first mounting stud 60 comprises a bosses 62,64 defined at its opposite ends. The boss 62 is slidably received in a bore 66 defined by the base 12. A set-screw 68 is used to secure the boss 62 in the bore 66. Alternatively, the first mounting stud 60 can be threadably secured to the base 12 or be secured by fasteners or be integral to the base as a one-piece construction or by a weld.

The first and second gooseneck members 40,50 are both fixedly secured to the first mounting stud 60. The boss 64 is closely slidably received in the bore 56 at the proximal end 52 of the second gooseneck member 50. A set-screw 58 or other fastener or another suitable means is used to fixedly secure the boss 64 in the bore 56. Similarly, at least a portion of the first mounting stud 60 is closely slidably received in the bore 46 of the first gooseneck member 40. A set-screw 48 or other fastener or another suitable means is used to fixedly secure the first mounting stud 60 in the bore 46. For aesthetics and to provide a good surface against which the set-screws 48,58 seat, the proximal end 42 of the first gooseneck member 40 is preferably surrounded by an inflexible sleeve member 34 as shown which is defined, e.g., from stainless steel. The set-screws 48,58 preferably pass through the sleeve member 34 and fixedly secure the sleeve member in position.

A second mounting stud 70 is secured to the distal end 24 of the shaft 20. More particularly, the second mounting stud 70 is fixedly secured to both the respective distal ends 44,54 of the first and second gooseneck members 40,50. In the illustrated embodiment, the second mounting stud 70 comprises a boss 72 that is closely slidably received in the bore 56 at the distal end 54 of the second gooseneck member 50. At least a portion of the second mounting stud 70 is closely and slidably received in the bore 46 at the distal end 44 of the first gooseneck member 40. A set-screw 74 or other fastener or another suitable means is used to fixedly secure the second mounting stud to the first and second gooseneck members 40,50. Here, again, it is desirable for aesthetic and functional purposes that an inflexible sleeve member 36 be provided and surround the distal end 44 of the first gooseneck member. As noted above, in addition to improving the appearance of the device 10, the sleeve member 36 provides a good surface against which the set screw 74 seats. The set-screw 74 passes through the sleeve member 36 and secures the sleeve member 36 in its operative position.

The snap-hook 32 is preferably secured to the second mounting stud 70 via fastener 80. More particularly, the fastener 80 is threadably or otherwise engaged with the second mounting stud 70. A stand-off bushing 84 spaces the snap-hook 32 from the stud 70 and two washers 86a, 86b or the like are located on opposite sides of the snap hook to trap the snap-hook 32 therebetween.

It is most preferred that the first and second gooseneck members 40,50 both be defined from spiral-wound stainless steel flexible tubing. Preferably, at least the first gooseneck member 40 is coated with a polymeric skin or film 38 (FIG. 1) that inhibits contamination and facilitates cleaning of the shaft 20 and that also improves the overall aesthetics of the device 10.

With continuing reference to the first and second coaxial gooseneck members 40,50, this dual gooseneck arrangement has been found highly preferably to use of a single gooseneck member for various reasons. First, the use of at least two coaxial gooseneck members 40,50 increases the resistance of the shaft 20 to bending, while still allowing a physician or other person to bend the shaft 20 selectively into any desired shape. Thus, the illustrated dual gooseneck arrangement for the shaft 20 increases the rigidity of the shaft 20 without rendering same unusable for infinite adjustment in accordance with the present invention. Secondly, the use of more than one gooseneck member 40,50 provides a redundancy that increases safety. If one of the gooseneck members 40,50 fails, the presence of the other gooseneck member 40,50 will prevent sudden and uncontrolled patient limb movement as could lead to complications with respect to the medical procedure being performed. Furthermore, it has also been found highly desirable to fixedly secure both the first and second gooseneck members 40,40 to both mounting studs 60,70 as shown and described. This reduces "play" or "slop" in the shaft 20 and provides added rigidity and added safety. Depending upon the exact conformation into which the shaft 20 is bent by an end-user, the shaft 20 will support up to about seven (7) pounds without undesired bending of the shaft under the weight of the patient's limb, i.e., it is preferred that the shaft 20 be formable into a shape that will support the weight of at least about seven (7) pounds.

With the foregoing in mind, those of ordinary skill in the art to which the invention pertains will appreciate that the shaft 20 can be bent manually in a selective manner so that the snap-hook 32 and limb support member 30 held thereby can be positioned as desired. In this manner, the shaft 20 is infinitely adjustable during use simply by direct manual manipulation. Also, owing to the bendable nature of the shaft 20, the shaft 20 will resiliently yield somewhat without moving out of its intended position so that the device 10 increases patient comfort.

Figure 5:
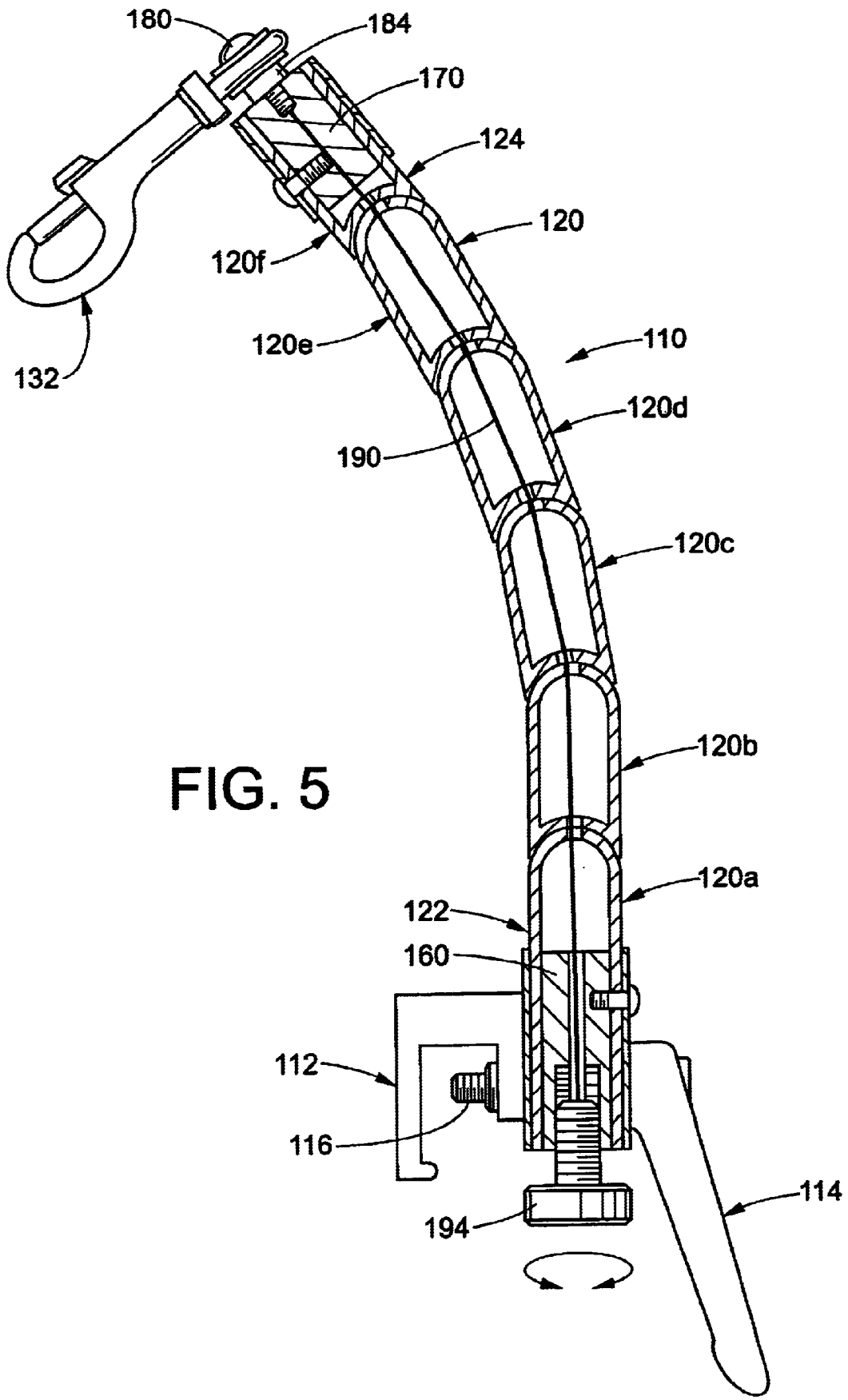

FIG. 5 illustrates a medical stirrup device 110 formed in accordance with an alternative embodiment of the present invention. Except as otherwise shown and described, the device 110 is identical to the device 10 and, thus, like reference numerals that are "100" greater than those used in FIGS. 1–4 are used to identify corresponding components.

The device 110 includes a gooseneck shaft 120 having a proximal end 122 and a distal end 124. The proximal end 122 of the shaft 120 is secured to the base 112 and a snap-hook 132 is secured to the distal end 124 of the shaft 120. The shaft 120, itself, comprises a series of interconnected links 120a–120f that articulate relative to each other. The links 120a–120f are preferably defined from stainless steel.

A cable 190 extends axially through the links 120a–120f. A proximal end 192 of the cable is coupled to a tensioning member 194 that is, in turn, secured to the shaft 120 or to the base 112 as shown. In the illustrated example, the tensioning member 194 is threaded into the first mounting stud 160. Rotation of the tensioning member 194 in a first direction increases the tension in the cable 190 while rotation of the tensioning member 194 in a second direction reduces tension in the cable 190.

When tension in the cable 190 increases, the links 120a–120f are drawn together so that friction between the links increases and the shaft 120 increases in rigidity. In contrast, when tension in the cable 190 is reduced, friction between the links 120a–120f decreases and the flexibility of the shaft 120 increases. The tensioning member 194 is used to control tension in the cable 190 and, consequently, the rigidity of the shaft 120. At one extreme, tension in the cable 190 is minimized and the shaft is freely bendable but is also too flexible to function as a medical stirrup device. At the other extreme, when tension in the cable 190 is maximized, the shaft 120 becomes rigid and inflexible and is not manually bendable or adjustable as required for an adjustable stirrup device.

Between these two extremes, the tension on the cable 190 can be set to provide a shaft 120 that is selectively bendable as desired but that is sufficiently rigid to support the weight of a pediatric patient's limb. Of course, using the device 110, it is possible for a physician or other person to selectively bend to the shaft 120 to the desired position and then to operate the tensioning member 194 to increase tension in the cable thereby causing the shaft 120 to become rigid and immovably fixed in the desired position.

A suitable material from which to define at least part of the shaft 120 is available commercially from Mediflex division of Flexbar Machine. Islandia, N.Y. and is sold under the trademark MEDIFLEX™.

The invention has been described with reference to preferred embodiments. Modifications and alterations will occur to those of ordinary skill in the art to which the invention pertains. It is intended that the appended claims be construed as encompassing all such modifications and alterations.

Having thus described the preferred embodiments, what is claimed is:

1. A medical stirrup device comprising:
    a base adapted for fixed securement to an associated support member;
    a gooseneck shaft member comprising a proximal end connected to said base and a distal end spaced from said base, said gooseneck shaft member being selectively manually bendable into a curvilinear operative shape and infinitely adjustable between an unbent linear position and a bendable limit of the gooseneck shaft member said gooseneck shaft member comprising a first tubular member defining a bore, and a second tubular member defining a bore, located in said first tubular member;
    a fastening element located at the distal end of said gooseneck shaft member;
    a limb support member for supporting a human limb in a desired position, said limb support member connected to said fastening element located at said distal end of said gooseneck shaft member and, a first mounting stud connected to said base, wherein both said first and second tubular members are connected to said first mounting stud.

2. The medical stirrup device as set forth in claim 1, wherein said gooseneck shaft member comprises a spiral-wound tubular member.

3. The medical stirrup device as set forth in claim 1, wherein said first and second tubular members are both spiral-wound tubular members.

4. The medical stirrup device as set forth in claim 1, wherein said first and second tubular members are co-axial relative to each other.

5. The medical stirrup device as set forth in claim 1, further comprising a polymeric film coating an exterior surface of said first tubular member.

6. The medical stirrup device as set forth in claim 1, wherein said first mounting stud is received in said bore of said first tubular member and wherein said first mounting stud defines a boss that is received in said bore of said second tubular member.

7. The medical stirrup device as set forth in claim 1, further comprising a second mounting stud connected to said distal end of said gooseneck shaft member, wherein said fastener is connected to said second mounting stud.

8. The medical stirrup device as set forth in claim 7, wherein said second mounting stud is received in a bore of said first tubular member, said second mounting stud defines a boss that is received in a bore of said second tubular member, and said first and second tubular members are both fixedly secured to said second mounting stud.

9. A method of supporting a human limb at a select desired position during a medical procedure, said method comprising:
    connecting a base of the stirrup device a claim 1 to a medical procedure table;
    placing a human limb in a limb support member that is connected to a shaft of the stirrup device; and,
    manually bending the shaft of the stirrup device in an infinitely adjustable manner to a desired shape corresponding to a desired location on the human limb.

\* \* \* \* \*